United States Patent
Tsubouchi et al.

(10) Patent No.: US 9,743,836 B2
(45) Date of Patent: Aug. 29, 2017

(54) EXCITATION, DETECTION, AND PROJECTION SYSTEM FOR VISUALIZING TARGET CANCER TISSUE

(75) Inventors: Takeshi Tsubouchi, Dexter, MI (US); Katsushi Inoue, Tokyo (JP)

(73) Assignees: Terumo Kabushiki Kaisha, Tokyo (JP); SBI Pharmaceuticals Co., Ltd., Tokyo (JP)

( * ) Notice: Subject to any disclaimer, the term of this patent is extended or adjusted under 35 U.S.C. 154(b) by 867 days.

(21) Appl. No.: 13/516,027

(22) PCT Filed: Dec. 20, 2010

(86) PCT No.: PCT/US2010/061188
§ 371 (c)(1),
(2), (4) Date: Jun. 14, 2012

(87) PCT Pub. No.: WO2011/084722
PCT Pub. Date: Jul. 14, 2011

(65) Prior Publication Data
US 2012/0259231 A1    Oct. 11, 2012

Related U.S. Application Data

(60) Provisional application No. 61/288,498, filed on Dec. 21, 2009.

(51) Int. Cl.
*A61B 5/00* (2006.01)
*A61N 5/06* (2006.01)
*A61B 18/00* (2006.01)

(52) U.S. Cl.
CPC .......... *A61B 5/0059* (2013.01); *A61B 5/0064* (2013.01); *A61B 5/0071* (2013.01);
(Continued)

(58) Field of Classification Search
CPC ... A61B 5/0059; A61B 5/0064; A61B 5/0071; A61B 2018/00904; A61B 5/0077; A61N 5/062; A61N 2005/0626
See application file for complete search history.

(56) References Cited

U.S. PATENT DOCUMENTS

| 4,162,405 A | 7/1979 | Chance et al. |
| 4,768,513 A * | 9/1988 | Suzuki .......................... 600/476 |

(Continued)

FOREIGN PATENT DOCUMENTS

| JP | H06125911 A | 5/1994 |
| JP | 2005021453 | 1/2005 |

(Continued)

OTHER PUBLICATIONS

Japan Office Action, Patent Application No. 2012-546097—Rejection of the Application, Mailing No. 284796, Mailing date Jul. 1, 2015.

*Primary Examiner* — Bo J Peng
(74) *Attorney, Agent, or Firm* — Darryl Newell; MacMillan, Sobanski & Todd LLC

(57) ABSTRACT

A system visually distinguishes diseased tissue from healthy tissue after a treatment is administered to a patient to provide different concentrations of a fluorescent marking substance between the diseased tissue and the healthy tissue. A light source illuminates the tissue with excitation light. A detector detects light returning from the tissue, and a controller characterizes the returning light according to a measured property indicative of the different concentrations. A light projector projects light having a predetermined cue in response to the characterization of the returning light.

11 Claims, 5 Drawing Sheets

(52) U.S. Cl.
CPC ............ *A61N 5/062* (2013.01); *A61B 5/0077* (2013.01); *A61B 2018/00904* (2013.01); *A61N 2005/0626* (2013.01)

(56) References Cited

U.S. PATENT DOCUMENTS

| | | |
|---|---|---|
| 4,930,516 A | 6/1990 | Alfano et al. |
| 5,644,429 A * | 7/1997 | Alfano et al. ................ 359/559 |
| 5,749,830 A * | 5/1998 | Kaneko et al. ............... 600/160 |
| 5,769,081 A | 6/1998 | Alfano et al. |
| 5,772,593 A | 6/1998 | Hakamata |
| 5,995,866 A | 11/1999 | Lemelson |
| 8,496,695 B2 | 7/2013 | Kang et al. |
| 2002/0062061 A1 * | 5/2002 | Kaneko et al. ............... 600/118 |
| 2005/0085732 A1 * | 4/2005 | Sevick-Muraca et al. ... 600/473 |
| 2006/0012872 A1 | 1/2006 | Hayashi et al. |
| 2007/0149882 A1 | 6/2007 | Wedel |
| 2008/0177184 A1 | 7/2008 | Goldman et al. |
| 2009/0043296 A1 * | 2/2009 | Foster et al. .................... 606/11 |
| 2009/0131800 A1 | 5/2009 | Liang |
| 2009/0221920 A1 | 9/2009 | Boppart et al. |
| 2010/0168586 A1 | 7/2010 | Hillman et al. |

FOREIGN PATENT DOCUMENTS

| | | |
|---|---|---|
| JP | 2005328990 A | 2/2005 |
| JP | 2006095166 | 4/2006 |
| JP | 2007047492 A | 2/2007 |
| JP | 2008149107 | 7/2008 |
| WO | 2004036284 A1 | 4/2004 |
| WO | 2007111408 A1 | 10/2007 |
| WO | 2009005748 A1 | 1/2009 |

* cited by examiner

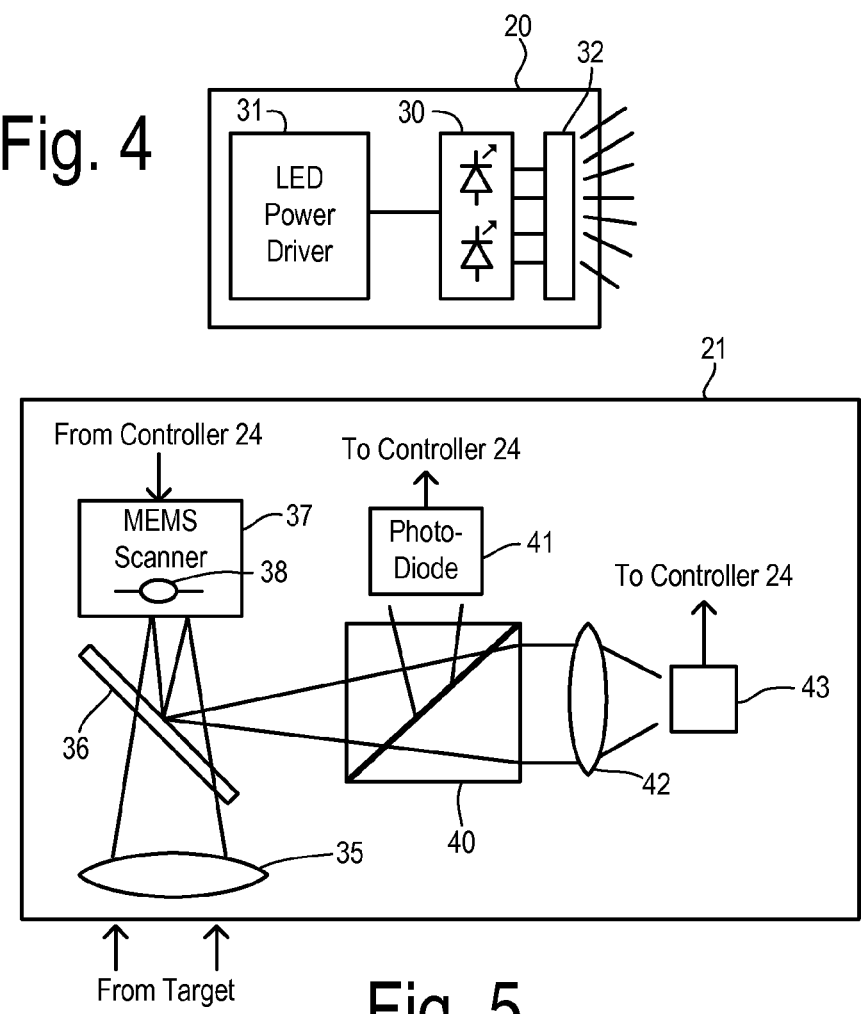
Fig. 4
Fig. 5
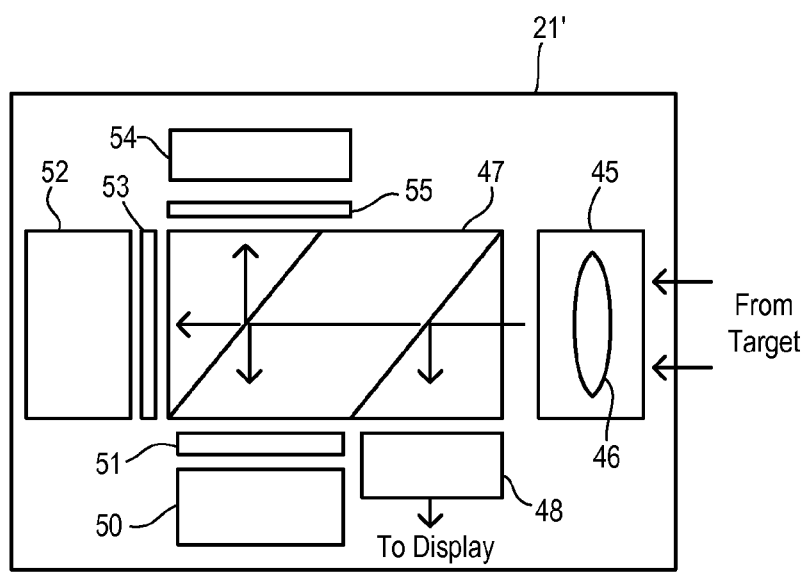
Fig. 6

EXCITATION, DETECTION, AND PROJECTION SYSTEM FOR VISUALIZING TARGET CANCER TISSUE

TECHNICAL FIELD

The present invention relates in general to optical detection of cancerous tissue with fluorescent markers, and, more specifically, to an optical system for visually highlighting marked tissues for excision by a surgeon.

BACKGROUND

Fluorescent markers have been used to differentiate between diseased and healthy tissues in connection with applying therapies such as surgical excision. Photodynamic substances have been used with properties that cause them to accumulate in tumor cells so that the fluorescence can be used to detect the cancer cells. One such substance is 5-aminolevulinic acid (5-ala) which is taken up by all cells but which is quickly eliminated by healthy cells but converts to a fluorescent substance protoporphyrin IX in cancer cells. During surgery to remove a tumor, excitation light is provided to the tissues, and the resulting fluorescent areas mark the cancer for removal. Another known photo-sensitizer substance is porfimer sodium, sold as Photofrin® by Axcan Pharma of Birmingham, Ala.

Due to the low concentrations of the photo-sensitive substance in the tissues, the amount of fluorescent light produced in the diseased tissues may be low. Thus, it may be difficult for a surgeon to see all the areas containing the marker substance. In surgeries of certain organs, such as the brain, it is desirable to ascertain precise boundaries between cancerous and healthy tissues so that all cancerous tissue can be removed without affecting any healthy tissue. To improve recognition, electronic systems with higher sensitivity than the human eye have been developed for sensing the areas that fluoresce. A sensed image of the fluorescing areas has been presented on a display screen or monitor. However, such systems still have a drawback in that the surgeon must estimate where the areas depicted on the monitor are actually located in the patient when performing the tissue removal.

SUMMARY OF INVENTION

The present invention has the advantage of providing a direct indication of the cancerous areas present in the patient. After electronically detecting the fluorescing areas, the present invention superimposes a coded image onto the patient that permits easy visual distinction between the cancerous and healthy tissues.

BRIEF DESCRIPTION OF DRAWINGS

FIG. 1 is a block diagram showing a first embodiment of a system of the present invention.

FIG. 4 is a block diagram showing one embodiment of an excitation module of the present invention.

FIG. 5 is a block diagram showing one embodiment of a detection module of the present invention.

FIG. 6 is a block diagram showing an alternative embodiment of a detection module of the present invention.

DESCRIPTION OF EMBODIMENTS

Figure 2:
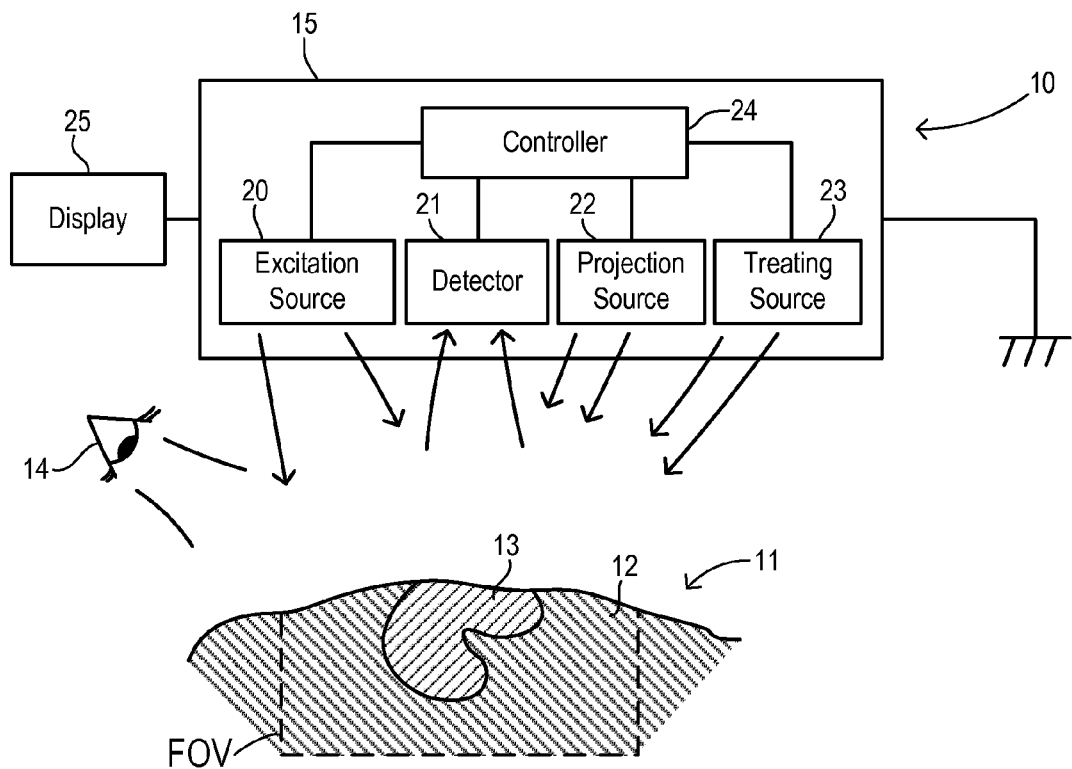
FIG. 2 illustrates target tissue with healthy and diseased tissue with an indication of the visible marking of diseased tissue obtained by the prior art.

The present invention is a form of photo dynamic diagnostic (PDD) in which a patient receives a photo-sensitizer substance resulting in a concentration of fluorescent material in diseased cancer cells. Referring to FIG. 1, a PDD system 10 is used while treating a patient 11. Patient 11 has healthy tissue 12 and diseased tissue 13 that are exposed during surgical intervention. A surgeon or other specialist visualizes the tissues using the naked eye 14. System 10 assists the surgeon by enabling better visualization of diseased tissue 13 within a field of view FOV of system 10.

System 10 includes several interacting modules which may be contained in a single housing 15 or may be separately constructed. A first module 20 includes an excitation source for generating light having a wavelength that excites the fluorescent substance in diseased tissue 13. When the photo-sensitizer is 5-ala, excitation source module 20 provides blue light with a wavelength of about 420 nM, which may be generated by a blue laser or LED. The blue light may be directed toward patient 11 either directly or through optics such as a lens or a diffuser.

A second module 21 comprises a detector that responds to the fluorescent emission of the photo-sensitizer substance on a localized basis across the tissue. As discussed below, the localization may be obtained using a scanning mirror, a CCD imager, or any other known technique to obtain separate measurements for each distinct area of tissue. Detector module 21 is responsive to the emission of red light, e.g., at a wavelength of 640 nM in the case of 5-ala.

A third module 22 comprises a projection source that responds to the localized data from detector module 21 in order to illuminate areas where diseased tissue is detected using a much more easily visualized lighting than the weak fluorescent emission from the diseased tissue. Preferably, the projection source light is characterized by a different color, intensity, or other light property, cue, or coding, thereby allowing the surgeon to discern the boundaries of the diseased tissue. In one preferred embodiment, projection source module 22 illuminates diseased tissue 13 using bright green light that is easily seen. Other examples of visual cues or image coding include time-varying intensity or color attributes of the projected light, or image patterns in the projected light.

A fourth module 23 may optionally be provided that includes a treating source for directing treating radiation to the spots where diseased tissue 13 is detected. Treating source module 13 may include a red laser that interacts with the marker substance in a manner that causes death of the diseased cells, as known in the art. A push button or other manual control would be provided so that the treating source is only energized when desired by the surgeon.

A controller 24 is coupled to modules 20-23 in order to coordinate operations and to process and share data. An optional display 25 can be connected to controller 24 in order to generate live images of tissue 12 and 13.

Figure 3:
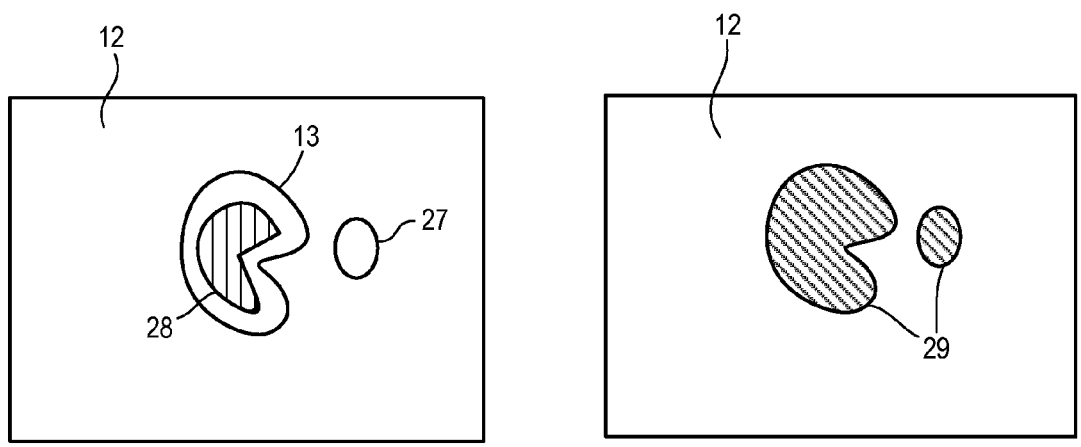
FIG. 3 illustrates target tissue with healthy and diseased tissue with an indication of the visible marking of diseased tissue obtained by the present invention.

FIG. 2 illustrates the visibility of fluorescent emissions using prior art methods. A patient has healthy tissue 12 and diseased tissues 13 and 27. All diseased tissues 13 and 27 contain fluorescent marker substance, but only area 28 includes a sufficient concentration to generate red light visible to the naked eye of the surgeon. With the additional projected illumination of the present invention, the surgeon sees green light 29 as shown in FIG. 3 that directly corresponds to all the diseased tissue. As long as any fluorescent marker remains at a concentration above a threshold, it will be detected by the system of the present invention and the projection source will continue to indicate the location(s) of remaining diseased tissue.

Excitation source module 20 is shown in greater detail in FIG. 4. A blue LED laser array 30 is powered by an LED power driver 31. Blue light from array 30 passes through a diffuser 32 for providing even excitation illumination to a target.

A first embodiment of detector module 21 is shown in greater detail in FIG. 5. Fluorescent and reflected emissions from a target are gathered by optics 35 (such as a lens) and pass through a half mirror 36 to a micro-electro-mechanical system (MEMS) scanner 37. MEMS scanner 37 includes a scannable mirror 38 that is deflected under control of controller 24 in order to reflect light received from a particular area (i.e., a pixel) of the target back to half mirror 36 and to a beam splitter 40. Some of the light from the pixel is directed to a photodiode 41 to support the creation of an image on the optional display. Another portion of the light emission received from the tissue pixel is provided by beam splitter 40 through a lens 42 to a spectrometer 43. Using a fast Fourier transform (FFT) or other known techniques, spectrometer 43 analyzes light received from the tissue pixel in order to determine whether the received light energy at the fluorescent wavelength exceeds a predetermined threshold indicative of the presence of diseased tissue. The resulting determination is provided from spectrometer 43 to controller 24.

FIG. 6 shows an alternative embodiment of detector module 21' in which full images are captured rather than using pixel scanning. Thus, light from the target is gathered by an optical system 45 which may contain a lens 46. Light passes to a beam splitter 47 directing a first portion of the light to a charge coupled device (CCD) 48 for forming an image that is sent to the (optional) display monitor. Another portion of the incoming light is directed by beam splitter 47 to a CCD 50 through a filter 51. Likewise, further portions of the light are directed to CCD 52 and 54 through filters 53 and 55, respectively. Image data from CCD 50, 52, and 54 are provided to controller 24 for analysis in order to determine presence of diseased tissues. Filters 51, 53, and 55 pass different wavelengths at or near the wavelength of the fluorescent emissions in order to detect pixels within the CCD images where the fluorescent emissions exceed a predetermined threshold as described in connection with FIGS. 7 and 8 below.

Figure 7:
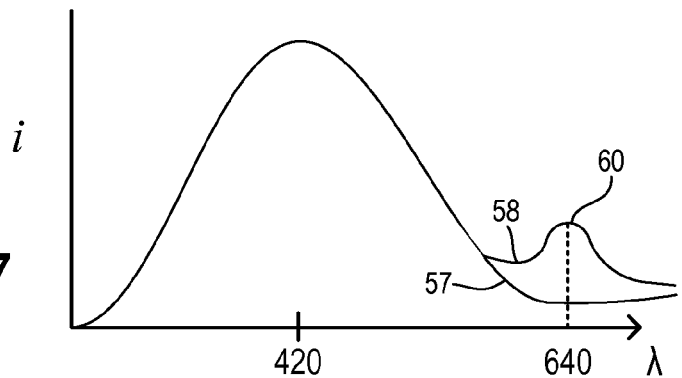
FIG. 7 is an energy plot showing a spectrum of light obtained from target tissue after excitation.

A spectrum of light reflected/emitted from the tissues while being illuminated by the blue light is shown in FIG. 7. The intensity of the light peaks at the fundamental wavelength of the blue illumination source, e.g., about 420 nM. For normal healthy tissue, the intensity of reflected light falls off into and through the red area of the spectrum as shown at 57. A different spectrum 58 results when diseased tissue containing the fluorescent marker is present. Thus, the spectrum increases to a secondary peak 60 at around a wavelength of 640 nM. The spectrum shown in FIG. 7 corresponds to an individual pixel or tissue area within the detected image. Each individual pixel has a respective spectrum according to its particular concentration of marker substance.

Figure 8:
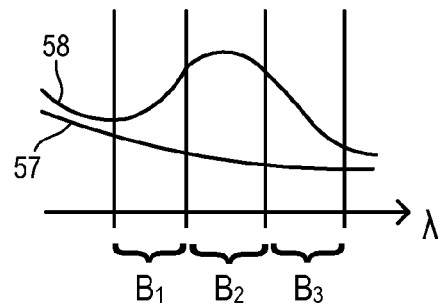
FIG. 8 shows bandwidth windows that can be used to detect whether fluorescing diseased tissue is present.

As shown in FIG. 8, separate passbands $B_1$, $B_2$, and $B_3$, for measuring the light energy received can be used to detect the presence of a peak in each respective spectrum. When the energy distribution exhibits the peak, then cancerous tissue is detected. Filters 51, 53, and 55, each correspond to a respective bandwidth $B_1$, $B_2$, and $B_3$, such that $B_2$ is centered on the peak emission wavelength. The resulting intensities (i.e., magnitudes) at each pixel in the CCD images can be compared in order to detect whether the corresponding peak is present. Thus, if the intensity for bandpass $B_2$ minus the intensity for bandpass $B_1$ is greater than zero and the intensity for bandpass $B_2$ minus the intensity for bandpass $B_3$ is also greater than zero, then a peak is detected and the corresponding pixel is marked as diseased. Otherwise, the corresponding pixel is marked as healthy.

Figure 9:
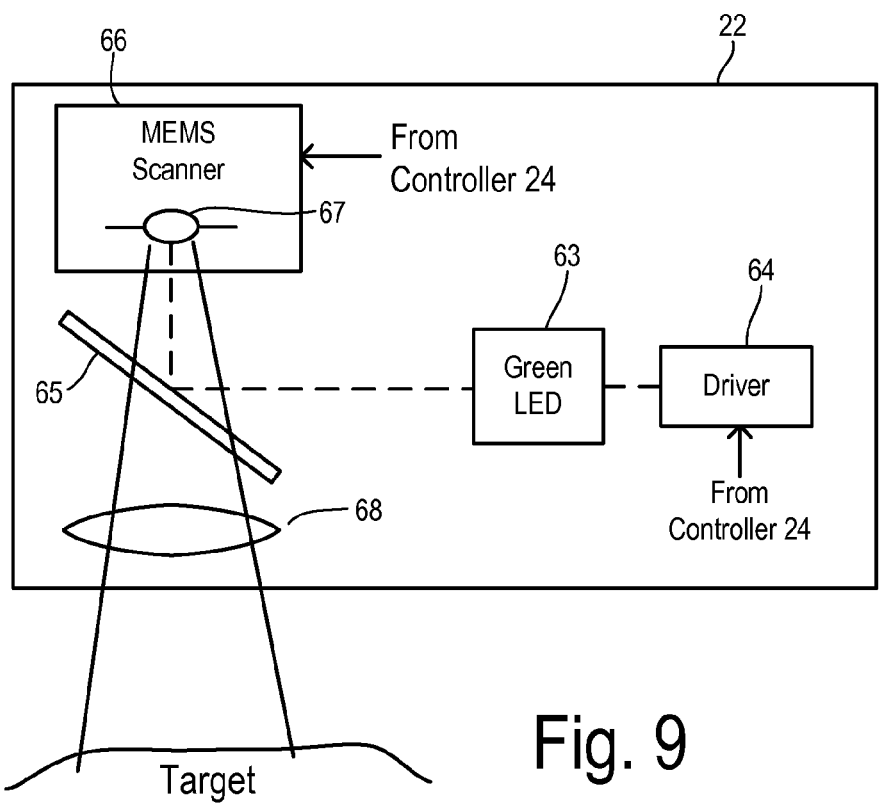
FIG. 9 is a block diagram showing one embodiment of a projection module of the present invention.

One embodiment of projection source module 22 is shown in greater detail in FIG. 9. A green light source 63 such as a green LED or other green laser source is driven by a power driver 64. Green light is directed to half mirror 65 and reflects to MEMS scanner 66 which has a tiltable mirror 67. Controller 24 positions mirror 67 according to pixels marked as diseased and activates driver 64 to turn on green source 63 to direct a beam of green light through mirror 65 and an optical system 68 to illuminate a corresponding pixel on the target tissue. Scanning mirror 67 may be controlled using horizontal and vertical trajectories crossing over all pixels, with green source 63 only being activated when crossing the appropriate pixels.

Figure 10:
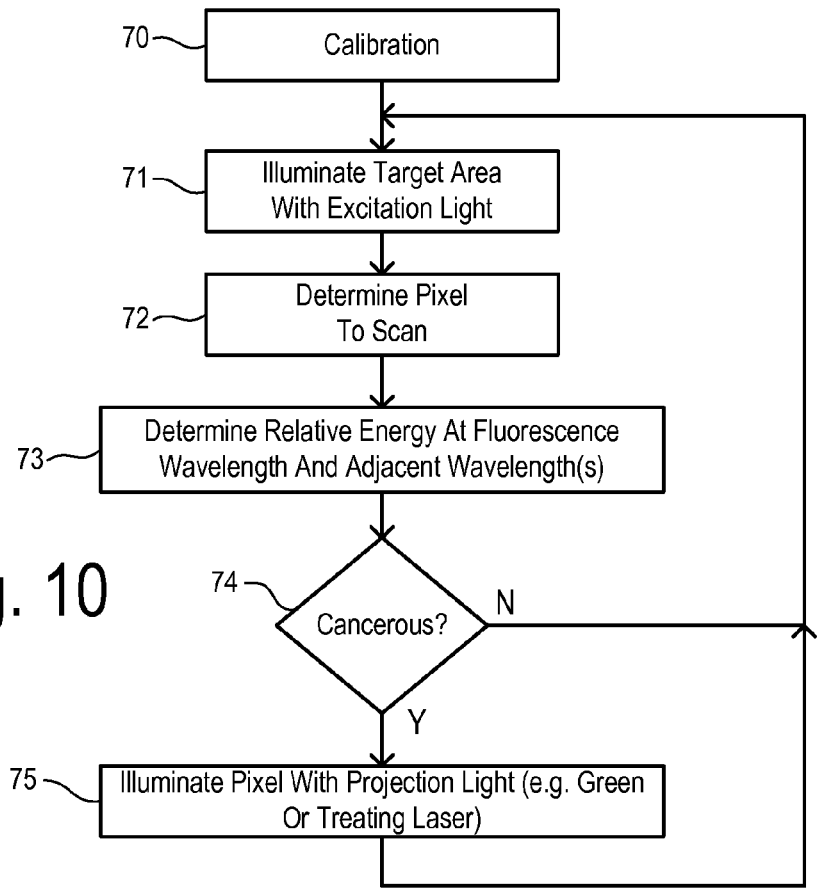
FIG. 10 is a flowchart of one preferred method of the present invention.

One preferred method of the invention will be described in connection with the flowchart of FIG. 10. In step 70, a position calibration is performed in order to align the projection source with the detection module. In one embodiment of the calibration, a pixel of green laser light from the projection source is scanned over a target area while monitoring the position of the resulting image of the green-illuminated pixel in the CCDs of the detector module. A calibration map is generated by the controller that correlates the coordinate spaces of the projector and the detector in order to accurately associate the corresponding pixels. In step 71, the target area is illuminated with the blue excitation light. In step 72, a determination is made as to which pixel should be scanned next. In response to the excitation light, tissue containing the marker substance generates a fluorescent emission. Relative energy at the fluorescent wavelength and adjacent wavelengths for the scanned pixel are determined in step 73. A determination is made in step 74 whether the relative energy levels indicate cancerous tissue. If not, then a return is made to step 71 to illuminate the target area with excitation light and to determine a next pixel to scan. If cancerous tissue is detected, than the corresponding pixel is illuminated with projection light in step 75 (e.g., either a green marker light or illumination by a treating laser). Thus, the green laser may be used to draw a pattern on the tissue corresponding to the areas where red fluorescent emission indicates diseased tissue.

Figure 11:
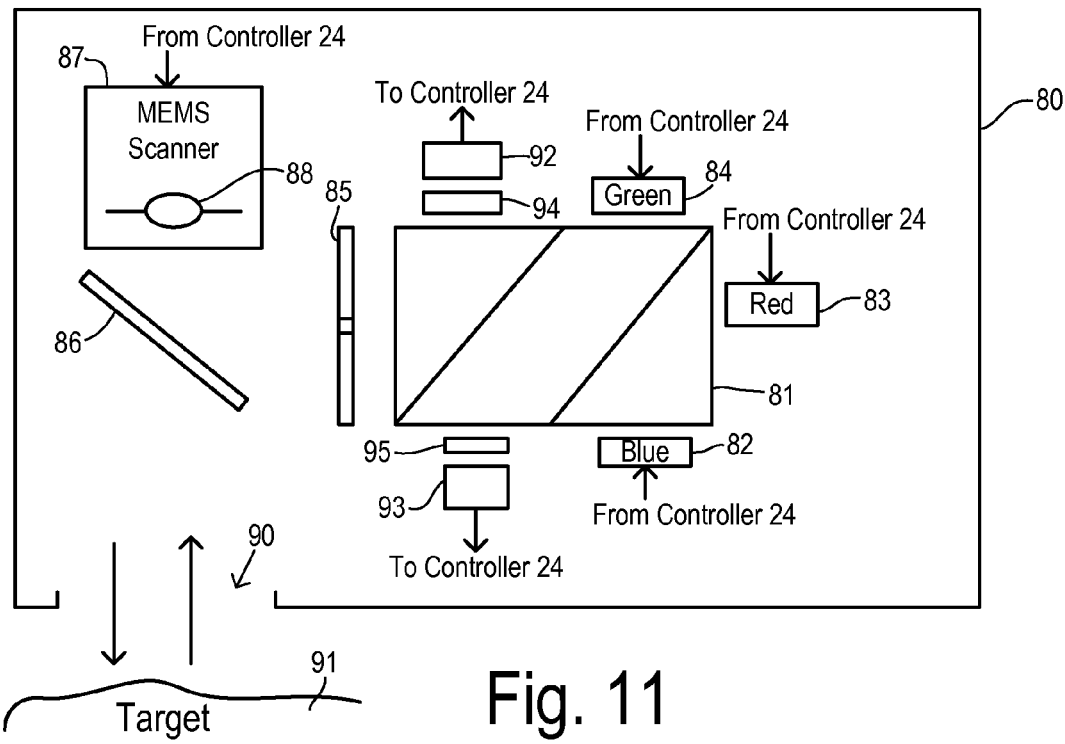
FIG. 11 is a block diagram showing an alternative system of the present invention that incorporates all the light generation and reception functions.

An alternative embodiment is shown in FIG. 11 wherein a PDD system 80 has all the various modules integrated into one unit. Thus, a beam splitter/combiner 81 receives laser light from a blue laser 82, a red laser 83, and a green laser 84 and directs it through a pinhole shade 85 or other optical system, and a half mirror 86 to a MEMS scanner 87. A scannable mirror 88 in MEMS scanner 87 directs the various laser lights through an aperture 90 (which may or may not contain further optics) to a target 91. A red laser used for photo dynamic therapy (PDT) may preferably correspond to the fluorescent frequency of the marker substance (e.g., 640 nM), but other frequencies may also be used. Beam splitter/combiner 81 may be comprised of a dichroic splitter, as appropriate.

Light from target 91 (including any fluorescent emission) passes through half mirror 86 to mirror 88 in MEMS scanner 87. Light for a presently scanned pixel reflects from mirror 88 to mirror 86 and through pinhole shade 85 into beam splitter/combiner 81. Some of the light is directed to photodetectors 92 and 93 through filters 94 and 95, respectively. One of filters 94 and 95 is centered on the fluorescent emission wavelength while the other is at an adjacent bandwidth. Using the device of FIG. 11, excitation, detection, projection marking, and treatment are performed on a pixel by pixel basis at a scanning rate sufficient to provide even illumination to the naked eye. Detection of a peak is performed by comparing energy at the bandwidth containing the fluorescent emission wavelength with energy at an adjacent bandwidth, preferably a passband which is below the bandwidth containing the fluorescent emission wavelength. In detecting peaks that correspond to diseased tissue, a predetermined threshold of about 1.3 for the ratio of energy in passband $B_2$ to the energy in passband $B_1$ can be used. Alternatively, the incoming light could be further split into another beam in order to compare passbands both below and above the fluorescent wavelength passband.

Figure 12:
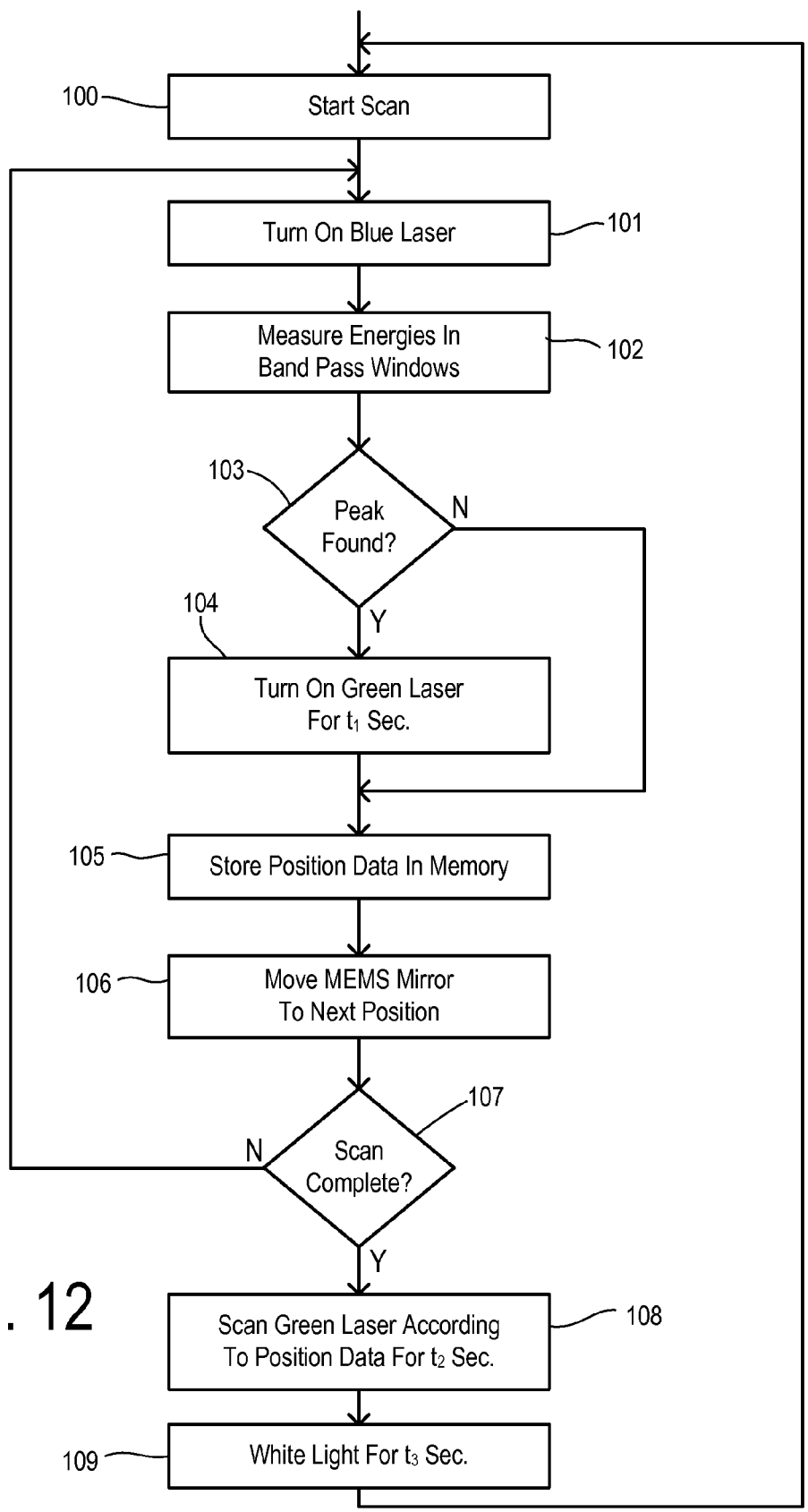
FIG. 12 is a flowchart of an alternative method of the invention that can be performed by the system of FIG. 11.

FIG. 12 shows a preferred method utilized by the system of FIG. 11. A scan is started in Step 100 (i.e., beginning at a first pixel). With the MEMS scanner set on a current pixel, the blue laser is turned on in Step 101 in order to provide excitation. The return energies in the bandpass windows are measured in Step 102, and a check is made to determine whether a peak is found for the current pixel in Step 103. If a peak is found then the green laser light is turned on in Step 104 for a predetermined time of $t_1$ seconds. If a peak is not found then Step 104 is skipped.

In Step 105, position data is stored in a memory of the controller. Specifically, for each pixel in a scanning area, the stored position data indicates whether a peak was detected. In Step 106, the scanning MEMS mirror is moved to the next position corresponding to the subsequent pixel. A check is made in Step 107 to determine whether a scan of the full image area has been completed. If not, then a return is made to Step 101 to continue with excitation by the blue laser. If the scan is completed, then a full projection scan of the green laser is performed in step 108 using the latest position data stored in memory. The projection scan may be continued for a time of $t_2$ seconds, wherein $t_2$ is greater than $t_1$. Thus, a first detection scan is performed while detecting the location of diseased tissue, wherein the detection scan also provides an initial illumination using the green laser of the diseased tissue. Once the full area has been detection scanned, the green laser alone may be scanned in order to ensure a bright image to be seen without interruption by the detection process. Due to the possibility of movement of the tissue or movement of the diagnostic system, periodic re-detection is desirable after the delay of $t_2$ seconds, wherein $t_2$ is chosen based on the fastest potential rate of movement that would give rise to the need to perform a re-scan. The value of $t_2$ may be about 250 ms, for example.

Optionally, a step 109 may be performed wherein white light illumination is generated (either by a separate source or by action of the colored sources together) for $t_3$ seconds to allow natural visualization of the area by the surgeon. Preferably, the while light illuminates the entire field of view of the device rather than just the diseased tissues.

The invention claimed is:

1. A system for visually distinguishing diseased tissue from healthy tissue wherein a treatment is administered to a patient to provide different concentrations of a fluorescent marking substance between the diseased tissue and the healthy tissue, the system comprising:
   a light source for illuminating the tissue with excitation light;
   a detector for detecting light returning from the tissue;
   a controller characterizing the returning light according to a measured property indicative of the different concentrations; and
   a light projector for projecting visible light onto the tissue having a predetermined visual cue localized in response to the characterization of the returning light so that boundaries of the diseased tissue are visually discernible.

2. The system of claim 1 wherein the detector detects light returning from respective pixel regions of the tissue, and wherein the light projector projects light with the predetermined visual cue to respective pixel regions identified by the controller as having a concentration of the fluorescent marking substance above a threshold.

3. The system of claim 1 wherein the detector is comprised of a photodetector and a scanning mirror for directing the light returning from the tissue to the photodetector.

4. The system of claim 3 wherein the photodetector is comprised of a charge-coupled device (CCD).

5. The system of claim 3 wherein the photodetector is comprised of a spectrometer.

6. The system of claim 3 wherein the scanning mirror is comprised of a micro-electro-mechanical system (MEMS).

7. The system of claim 1 wherein the light projector is comprised of a light source for projecting light of a predetermined color and a scanning mirror for directing the light of a predetermined color to respective pixel regions identified by the controller as having a concentration of the fluorescent marking substance above a threshold.

8. The system of claim 1 wherein the measured property characterized by the controller corresponds to an energy of returning light for respective pixel regions in the tissue.

9. The system of claim 1 wherein the controller uses a fast Fourier transform to analyze the returning light to determine whether energy at a fluorescent wavelength of the marking substance present in respective pixel regions of the tissue exceeds a predetermined threshold.

10. The system of claim 1 wherein the detector is comprised of filters for filtering the returning light according to a first passband including a fluorescent wavelength of the marking substance and a second passband including wavelengths adjacent the fluorescent wavelength, and wherein the controller compares energies of the returning light of the first and second passbands in order to determine the different concentrations.

11. The system of claim 1 further comprising a treating laser for photo dynamic therapy (PDT) of the same tissue that receives projected light having the predetermined cue.

* * * * *